United States
Govignon

4,023,189

May 10, 1977

[54] WIDE ANGLE FUNDUS ILLUMINATION AND PHOTOGRAPHY APPARATUS

[75] Inventor: Jacques P. Govignon, Malden, Mass.
[73] Assignee: Varian Associates, Palo Alto, Calif.
[22] Filed: Mar. 29, 1974
[21] Appl. No.: 455,975
[52] U.S. Cl. .............................. 354/62; 350/183; 351/6; 351/7
[51] Int. Cl.² ........................................ G03B 29/00
[58] Field of Search .......... 354/62; 350/183; 351/6, 351/7

[56] References Cited
UNITED STATES PATENTS

| | | | |
|---|---|---|---|
| 3,016,000 | 1/1962 | Noyori | 351/7 X |
| 3,259,039 | 7/1966 | Okajima | 354/62 X |
| 3,437,398 | 4/1969 | Muller | 350/183 X |
| 3,770,342 | 11/1973 | Dudragne | 351/7 |
| 3,780,979 | 12/1973 | Guillebon | 351/7 X |

*Primary Examiner*—Monroe H. Hayes
*Attorney, Agent, or Firm*—Thomas C. Stover, Jr.

[57] ABSTRACT

A wide angle instrument for illuminating, observing and photographing the fundus of the eye is provided. The instrument has a focus tube containing spaced decollimating and objective lenses with an adjustable aperture diaphragm positioned therebetween, which tube projects a glare-reducing entrance pupil on the eye examined and maintains the position and size thereof while the instrument is being focused by moving the focus tube relative to the eye examined to focus on the fundus.

18 Claims, 4 Drawing Figures

WIDE ANGLE FUNDUS ILLUMINATION AND PHOTOGRAPHY APPARATUS

FIELD OF THE INVENTION

This invention relates to wide angle illumination of an object, particularly illumination of an object for image reproduction thereof.

THE PRIOR ART

Although illumination of objects, e.g. the eye interior for viewing and picture taking is known, such devices have not provided for reduced glare, wide-angle illumination and picture taking thereof. The means for taking pictures of the fundus of the eye have provided narrow angle illumination and observation, e.g. 60° to 70°, and a number of photographs therefrom from 30° to 45° only, which then must be assembled to produce a composite picture of the eye. Further, these systems have been illuminated through the lens system that receives the image, resulting in viewing and pictures partially obscured by glare reflected in the lens system. Moreover, movement of the camera lens unit relative to the eye has been required to focus the same on the fundus thereof.

There is, therefore, a need and market for a device that substantially overcomes the above shortcomings to provide clear wide-angle illumination, observation and photographs of the fundus.

There has now been discovered a wide-angle observation system that illuminates the fundus of an eye positioned proximate thereto, a system that can project a glare-reducing entrance pupil on the lens of the eye and maintain such glare shield while being focused on the fundus, which focusing is accomplished without moving the camera relative to such eye.

SUMMARY

Broadly, the present invention provides an illuminated reduced-glare, image receiver for viewing an object comprising, means for illuminating said object, a first lens means mounted proximate the illuminated object for directing the light field reflected therefrom into a beam having diverging and converging rays;

a collimating lens means mounted on the axis of said beam and spaced from said first lens so that the intermediate image of the beam transmitted from said first lens is positioned therebetween, which lens lessens the divergence of the beam rays passing therethrough;

a focusing lens assembly positioned following said collimating means, in the path of said light beam and axially moveably mounted with respect thereto, said focusing lens assembly having decollimating lens means mounted in fixably spaced relationship to a diaphragm and objective lens means mounted proximate said diaphragm on the axis of said beam; and an image receiving means positioned on the remote side of said objective lens means for receiving said image such that the beam from said collimating lens means enters said focusing lens assembly through the decollimating lens means which directs the rays of said beam to said objective lens means through said diaphragm, which reduces glare components of said beam; at least some of the elements of the focusing lens assembly being moved along the beam until said beam is focused by the objective lens means on said image receiving means.

DESCRIPTION

The invention will become more apparent from the following detailed specification and drawings in which.

Figure 1:
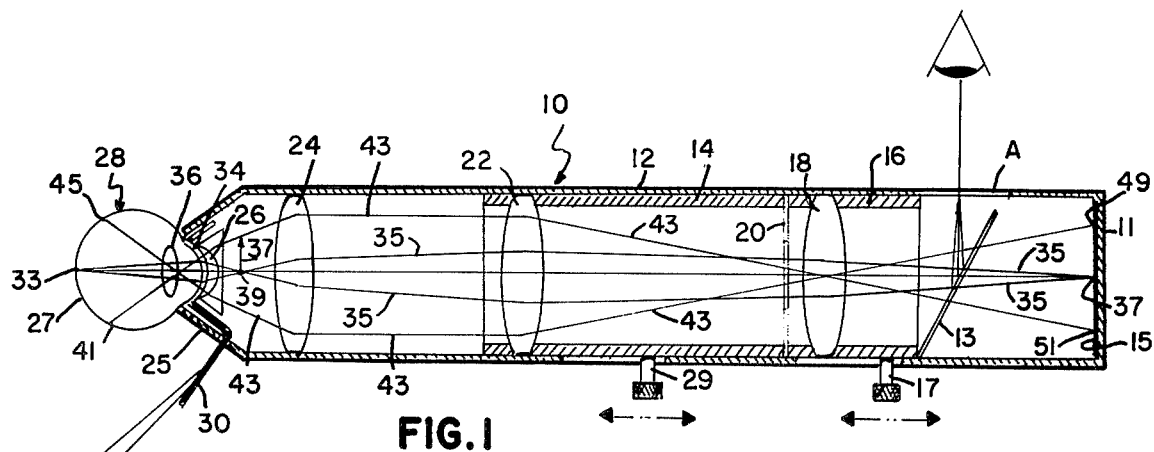
FIG. 1 is an elevation schematic view of the image receiver embodying the present invention.

Referring now to the drawings, the image receiver embodying the invention 10 includes camera 11 mounted at the rear end of main housing 12, shown in FIG. 1. At the forward end of the housing 12 is mounted objective lens cone 25 which contains foremost, as the first lens means, contact lens 34 and objective lens means 26 therebehind as shown in FIG. 1. The contact lens 34 is positioned in close proximity with the cornea of the eye to be observed. The fundus 27 of the eye 28 is illuminated by optic fiber bundle 30 which spreads into fibers mounted around the peripheral portion of the contact lens 34 at the rear side thereof, which fibers project a beam which illuminates a wide field of the fundus, also shown in FIG. 1.

Figure 2:
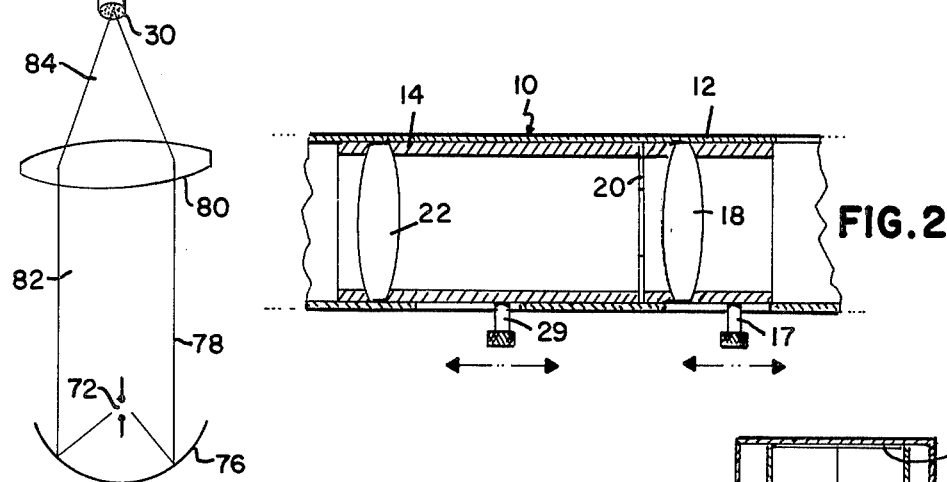
FIG. 2 is a sectional elevation view of a portion of the embodiment of FIG. 1.

Behind the objective lens means 26 is collimating lens means 24 followed by focus tubes 14 and 16 which are axially moveably mounted within the housing 12 as shown in FIG. 2. The focus tube 14 has mounted at the forward end thereof, decollimating lens means 22, spaced from adjustable aperture diaphragm 20, which is mounted at the rear end of such tube as shown in FIGS. 1 and 2. The focus tube 14 is moveable by knob 29. The focus tube 16 has objective lens means 18 mounted thereon and is moveable by knob 17 shown in FIG. 2. The knobs 17 and 29 extend through narrow slots in the housing 12.

Behind the focus tube 16, within the housing 12 is positioned beam splitter 13 and finally the image receiving device, e.g. film transport device, or camera 11 as shown in FIG. 1.

In operation, the head of the patient is positioned on a chin rest (not shown) and the entire image receiver 10 is brought into position proximate or in contact with the cornea of the patient's eye 28. The illuminating light is activated and travels through the optic fibers to project a beam which illuminates the fundus 27 of the eye 28 in a wide field. The beam 35, e.g. from point 33 on the fundus 27, then reflects back through the eye lens 36, through the pupil and the contact lens 34, through objective lens means 26 where the light beam converges to focal point 39 to form an intermediate image, thence diverges to collimating lens means 24, where the beam is rendered less divergent and directed rearwardly toward the focusing tube 14. The beam enters the focusing tube 14 through the decollimating lens means 22, which renders components of the beam less divergent and nearly parallel and directs such beam rearwardly through the diaphragm 20 (which reduces or blocks glare components of the beams) to the objective lens means 18 which converges the beam to a point or zone 37 on the image receiving means, e.g. film 15 of camera 11. In another example, points 41 and 45 on the fundus 27 reflect, respectively, illumination field rays 43, which are parallel between lens means 24 and 22 and pass through the respective lenses to points 49 and 51 on the camera film 11 as shown in FIG. 1. The focusing tubes 14 and 16 are moved within the housing 12 along the beam or beams until such beam is focused by the objective lens means 18 of the tube 14 on the camera 11 as seen by the observer at portal A thereof.

The focusing tubes 14 and 16 can be moved together or separately to obtain the desired focusing on the target area. For example, the tubes 14 and 16 can be moved as a unit or tube 14 can be moved relative to tube 16.

When proper illumination and focusing of the fundus 27 of the eye 28 is achieved, bright light can be beamed or pulsed into the fundus 27 through the same fiber optics 30 for examination and/or photography purposes to obtain well defined wide-angle pictures of such fundus. Accordingly the arc lamp 72 backed by the concave reflector 76 projects a beam 82 and 84 through focusing lens 80 to the fiber bundle 30 and thence to the fundus 27 of the eye 28 as shown in FIG. 1. Means (not shown) turn the lamp 72 on and off as desired.

Figure 3:
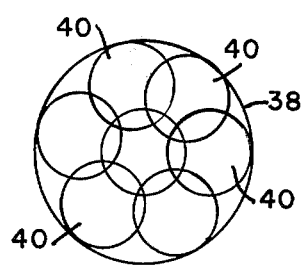
FIG. 3 is a facsimilie of the field of view of the fundus of the eye received by the image receiver embodying the present invention.

An example of the advance in the art of such pictures is shown in FIG. 3, wherein a 100° field of view 38 of the fundus which can be observed and photographed by the image receiver of the present invention is compared with the 45° field of view 40 of such fundus obtained by the most advanced fundus cameras. These 45° cameras require a succession of photographs to cover by composite, the 100° field which can be clearly photographed in one shot by the wide-angle camera embodying the present invention.

Thus, the image receiver of the invention provides for wide-angle illumination, focusing, observation and photography of objects including the fundus of the eye.

The image receiver embodying the invention, e.g. the wide-angle fundus camera, has the advantageous feature that it can be focused on the patient's eye or other object by means of the moveable focus tube without having to move the camera relative to the subject eye or the observing eye. A further advantageous feature of the image receiver of the invention is that the adjustable aperture diaphragm in the focus tubes "projects" an entrance pupil through the lens system onto the pupil of the eye examined. The projected pupil can be adjusted to a suitable diameter to permit viewing of the wide field of the fundus of the eye and yet small enough to screen out glare and haze of reflected light emerging through the eye to the image receiver for clear observation of the fundus without glare and haze interference. The specific advantage of this feature of the present invention is that once the projected pupil of a proper size is established on the eye examined (e.g. the eye lens 36 of FIG. 1), the size and position of this projected pupil is maintained even while the wide-angle camera is being focused by moving one or both focus tubes. Thus, the projected pupil from the adjustable aperture diaphragm remains constant while the focus tube or tubes are moved to obtain a sharp image for the image receiver of the invention.

The diaphragm of the invention is fixably mounted in spaced relationship with (and behind) said decollimating lens means and preferably at the focal point thereof, as illustrated, for example, in FIG. 1.

With respect to the objective lens means, said diaphragm can be located among the objective lenses (of the objective lens means) at the rear of the focus tube. Preferably, such diaphragm is located forward of such objective lenses or lens, e.g. forward of lens 18, in FIG. 1, to screen out glare and haze components of the light beam. When such diaphragm is forward of the objective lens means, advantageously, it should be proximate such lens means since the lens diameter of the objective lens means must be larger as the diaphragm is moved away therefrom.

The first lens means of the image receiver of the invention need not have a contact lens mounted thereon, since the unit may be spaced within a short distance of the eye, e.g. one to two millimeters or more, or it may contact the surface of such eye. Preferably, however, the first lens means does have mounted foremost a contact lens so that it may be brought comfortably in contact with such eye over the cornea thereof or be spaced a short distance therefrom, e.g. up to one or two millimeters more therefrom.

The type of contact lens employed in the present invention is preferably a corneal lens (single curve) as opposed to a scleral lens (multi-curve) which conforms closely to the eye surface contours. Particularly preferred is a corneal lens of 8.5 to 10 millimeters in diameter. The corneal lens can function in contact with the eye or spaced therefrom as stated above. The scleral lens functions effectively only in contact with the eye. These contact lenses are preferably of near zero refractive power and are of optical quality, preferably of transparent plastic.

As previously stated, the means for illuminating the interior of the eye preferably does not pass through the viewing or observation lens system except as necessary to enter the pupil of the eye at the periphery thereof. Preferably, the light is beamed into such eye through fiber optics spaced around and behind the lens nearest the pupil of the eye, e.g. the contact lens. In sum, for picture taking of the fundus of the eye, illuminating or aiming light and a flash system are projected into the fundus through the same fiber bundle and do not pass through the lens system, which further reduces glare. In other words, the illumination beams are separate from the viewing or camera beams. While the above fiber optic lighting system for illuminating the eye interior is preferred, other lighting systems may be employed within the scope of the present invention, including illuminating systems which beam light through the viewing or observation lens system, if desired.

Although various lamps can be employed in illuminating and for bright or flash lighting of the fundus of the eye, the lamp for bright lighting of the fundus is preferably a Xenon arc lamp with a concave (including elipsoidal or parabolic) reflector, preferably a parabolic reflector, an preferably with the electrodes of the arc lamp positioned so that the axes thereof coincide with the axis of the reflector.

The first lens means at the forward end of the image receiver can be one or more lenses which magnify the light beam received, i.e. project a converging or diverging beam. The second or collimating light lens means can be one or more lenses which convert the divergent beam into a less divergent or a parallel light beam.

The focusing lens assembly can be the focusing tubes, as described above and can also be any system having two or more spaced lens means and a diaphragm which are axially moveable, separately or together, with respect to the second or collimating lens means in the path of the light beam issuing therefrom, which focus a beam as described above on an image receiving means, e.g. camera, observing eye, screen and the like. The focusing lens assembly, as stated, can be a tube or other lens carriage, e.g. an open network which supports the spaced lens means and diaphragm, a bar or rod supporting one or both lens means, a rectangular tube or any other shape which can serve to hold such lens means and diaphragm in spaced relationship, provided that such lens means are axially moveable with respect to the second or collimating lens means.

The focusing lens assembly can have, at the forward portion thereof, as decollimating lens means, one or more lenses mounted thereon and at the remote end thereof, as objective lens means, one or more lenses mounted thereto with an adjustable aperture diaphragm mounted among the objective lenses or in front of same, proximate thereto.

Between the objective lens means of the focusing lens assembly and the image receiving means, can be positioned a beam splitter, which, as discussed above, directs a portion of the beam to an image receiving means, e.g. a camera, and directs another portion of said beam to another image receiving means, e.g. a viewing portal for an observer, a TV or other camera, a scope and the like. The beam splitter can be a prism and a flat piece of glass of equivalent index of refraction or a cube beam splitter. The beam splitter can be dispensed with if desired. A reflex camera, where employed, provides a viewing portal through the camera lenses.

Other objects or articles besides the interior of the eye can be focused upon and observed through the image receiver of the present invention. Objects, where removing glare for a clear picture is desirable, can be readily viewed and photographed through the apparatus of the present invention, e.g. the interior of locks, insects and miniature electronic equipment, as well as larger objects where it is convenient to be able to focus the image receiver without having to move the overall assembly relative to the object to be observed or photographed. Preferably, the image receiver embodying the present invention is highly suited for wide-angle illumination, observation and photographing of the fundus of the eye with sharply focused, glare-free clarity.

The image receiving means at the end of the image receiver can include the observation eye, film, TV, motion and still cameras and scopes and measuring devices, e.g. reflectometer or a combination thereof.

In the wide-angle camera embodying the present invention, illumination, observation and photographing of the fundus with a field of view of between 80° to 150° and usually 100° or more is obtained in sharp clarity.

Figure 4:
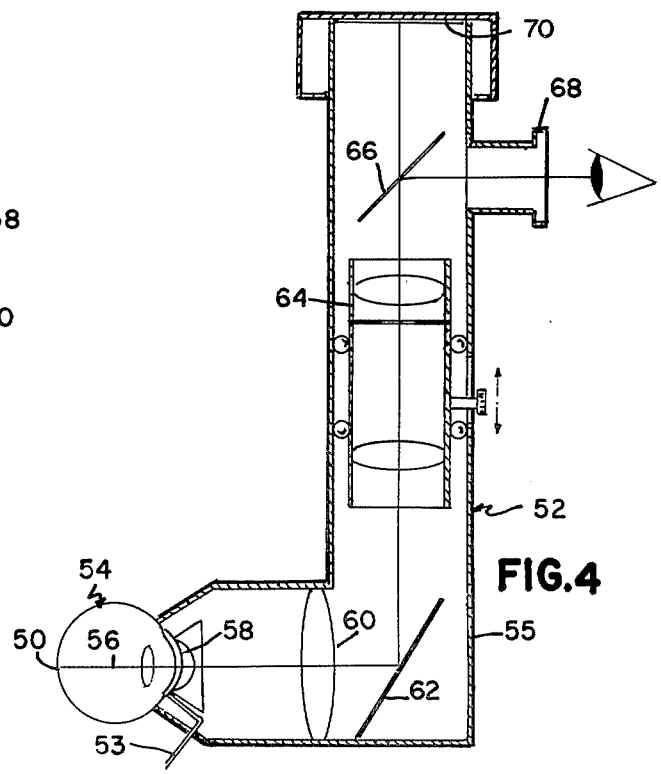
FIG. 4 is a partially schematic elevation view of another image receiver embodying the present invention.

In addition to single axis alignment of the lens components of the image receiver of the present invention, various other multi-axes lens alignment embodiments can be provided within the scope of the present invention. Thus, by use of reflective means the lens components of the invention can be positioned at suitable angles to define a more compact unit where desired. For example, image receiver 52 has, positioned in housing 55, illuminating means 53 which directs light to the fundus 50 of eye 54 as shown in FIG. 4. The fundus 50 reflects light beam 56 through first lens means 58, through collimating lens means 60, thence to mirror 62 which directs the beam at a different axis to focusing lens assembly 64 (having decollimating lens means, an adjustable aperture diaphragm and an objective lens means) to beam splitter 66, which angles a portion of the beam to viewing portal 68, while permitting passage therethrough of the remainder of the beam to camera film 70, as shown in FIG. 4.

What is claimed is:

1. An illuminated, reduced-glare, image receiver for viewing an object comprising, means for illuminating said object, a first lens means mounted proximate the illuminated object for directing the light field reflected therefrom into a beam having diverging and converging rays a collimating means mounted on the axis of said beam and spaced from said first lens so that the intermediate image of the beam transmitted from said first lens is positioned therebetween, which lens lessens the divergence of the beam rays passing therethrough; a focusing lens assembly positioned following said collimating lens means, in the path of said light beam and axially moveably mounted with respect thereto, said focusing lens assembly having decollimating lens means mounted in fixably spaced relationship to a diaphragm and objective lens means mounted proximate said diaphragm on the axis of said beam; and an image receiving means positioned on the remote side of said objective lens means for receiving said image such that the beam from said collimating lens means enters said focusing lens assembly through the decollimating lens means which directs the rays of said beam to said objective lens means through said diaphragm, which reduces glare components of said beam; at least some of the elements of the focusing lens assembly being moved along the beam until said beam is focused by the objective lens means on said image receiving means.

2. The image receiver of claim 1 wherein said focusing lens assembly has said decollimating lens means, said diaphragm and said objective lens mounted in fixed relationship to move together along the axis of said beam.

3. The image receiver of claim 1 wherein said focusing lens assembly has said decollimating lens means and said diaphragm mounted in fixed relationship to move together along the axis of said beam independently from said objective lens.

4. The image receiver of claim 1 wherein said focusing lens assembly is mounted on a carriage which is axially moveable with respect to said collimating lens means and said image receiving means and said diaphragm is mounted at the focal point of said decollimating lens.

5. The image receiver of claim 1 wherein said focusing lens assembly is a focus tube axially moveable with respect to said collimating lens means and said image receiving means.

6. The image receiver of claim 1 wherein each lens means is a plurality of lenses mounted in series.

7. The image receiver of claim 1 wherein said first lens means has a plurality of lenses mounted at the smaller end of a conical housing.

8. The image receiver of claim 1 wherein an adjustable aperture diaphragm is mounted between a pair of lenses in said objective lens means.

9. The image receiver of claim 1 wherein an adjustable aperture diaphragm is mounted between said decollimating lens means and said objective lens means.

10. The image receiver of claim 1 wherein said object is the fundus of the eye, said first lens means having, foremost, a contact lens mounted thereto, said contact lens having a plurality of optical fibers mounted around and on the rear surface of the contact lens proximate the rim thereof, means for placing said contact lens in close proximity with the pupil of said eye and means for transmitting light through said fibers into said eye to illuminate the fundus thereof.

11. The image receiver of claim 10 wherein said contact lens is a corneal contact lens which can be employed in contact with, as well as in, spaced proximity with the cornea of the eye.

12. The image receiver of claim 10 wherein bright means emits high intensity light to said fibers for transmission therethrough (for transmitting high intensity light through said fibers is provided) to enable picture taking of said fundus.

13. The image receiver of claim 12 wherein said bright means is an arc lamp backed by a concave reflector.

14. The image receiver of claim 12 wherein said bright means is an xenon arc lamp backed by a parabolic reflector.

15. The image receiver of claim 12 wherein said bright means is an xenon arc lamp backed by a parabolic reflector, the electrodes thereof being mounted so that their axes coincide with the axis of the reflector.

16. The image receiver of claim 12 wherein said bright means is an xenon arc lamp backed by a parabolic reflector, said contact lens is a corneal lens 8.5 to 10 mm in diameter and said focusing lens assembly projects a pupil on the crystaline lens of the eye which pupil can be adjusted to the desired size then maintained constant while the focusing lens assembly is moved into focus on the fundus of said eye.

17. The image receiver of claim 1 wherein said image receiving means is a camera.

18. The image receiver of claim 17 wherein a beam splitter is mounted between said objective lens means and said camera for directing part of the beam issuing from said objective lens means to a viewing portal.

* * * * *